United States Patent [19]
Huxley et al.

[11] Patent Number: 5,917,090
[45] Date of Patent: Jun. 29, 1999

[54] MATRIX METALLOPROTEINASE INHIBITORS

[75] Inventors: Philip Huxley; Fionna Mitchell Martin; Andrew Miller; Zoe Marie Spavold, all of Oxford, United Kingdom

[73] Assignee: British Biotech Pharmaceuticals Ltd., Oxford, United Kingdom

[21] Appl. No.: 08/981,221

[22] PCT Filed: Jul. 1, 1996

[86] PCT No.: PCT/GB96/01578

§ 371 Date: Dec. 19, 1997

§ 102(e) Date: Dec. 19, 1997

[87] PCT Pub. No.: WO97/02239

PCT Pub. Date: Jan. 23, 1997

[51] Int. Cl.⁶ .................................................. A01N 37/28
[52] U.S. Cl. .......................... 562/623; 562/621; 514/575
[58] Field of Search ................... 562/621, 623; 514/575

[56] References Cited

U.S. PATENT DOCUMENTS

| | | |
|---|---|---|
| 3,468,936 | 9/1969 | van der Burg . |
| 4,599,361 | 7/1986 | Dickens et al. . |
| 4,996,358 | 2/1991 | Handa et al. . |
| 5,183,900 | 2/1993 | Galardy et al. . |
| 5,256,657 | 10/1993 | Singh et al. . |
| 5,270,326 | 12/1993 | Galardy et al. . |
| 5,300,501 | 4/1994 | Porter et al. . |
| 5,300,674 | 4/1994 | Crimmin et al. . |
| 5,304,549 | 4/1994 | Broadhurst et al. . |
| 5,569,665 | 10/1996 | Porter et al. . |
| 5,643,964 | 7/1997 | Dickens et al. . |

FOREIGN PATENT DOCUMENTS

| | | |
|---|---|---|
| 0231081 | 8/1987 | European Pat. Off. . |
| 0274453 | 7/1988 | European Pat. Off. . |
| 0489577 | 6/1992 | European Pat. Off. . |
| 0489579 | 6/1992 | European Pat. Off. . |
| 0497192 | 8/1992 | European Pat. Off. . |
| 0574758 | 12/1993 | European Pat. Off. . |
| 0575844 | 12/1993 | European Pat. Off. . |
| 9005716 | 5/1990 | WIPO . |
| 9005719 | 5/1990 | WIPO . |
| 9102716 | 3/1991 | WIPO . |
| 9209563 | 6/1992 | WIPO . |
| 9213831 | 8/1992 | WIPO . |
| 9217460 | 10/1992 | WIPO . |
| 9222523 | 12/1992 | WIPO . |
| 9309090 | 5/1993 | WIPO . |
| 9309097 | 5/1993 | WIPO . |
| 9320047 | 10/1993 | WIPO . |
| 9324449 | 12/1993 | WIPO . |
| 9324475 | 12/1993 | WIPO . |
| 9402446 | 2/1994 | WIPO . |
| 9402447 | 2/1994 | WIPO . |
| 9410990 | 5/1994 | WIPO . |
| 9421612 | 9/1994 | WIPO . |
| 9421625 | 9/1994 | WIPO . |
| 9424140 | 10/1994 | WIPO . |
| 9425434 | 11/1994 | WIPO . |
| 9425435 | 11/1994 | WIPO . |
| 9519961 | 7/1995 | WIPO . |

OTHER PUBLICATIONS

Conway et al, *The Journal of Experimental Medicine*, vol. 182, pp. 449–457, Aug. 1995.

DiMartino et al, *Annals of the New York Academy of Sciences*, vol. 732, pp. 411–413, 1994.

Gijbels et al, *J. Clin. Invest.*, vol. 94, No. 6, pp. 2177–2182, Dec. 1994.

*Primary Examiner*—Brian M. Burn
*Assistant Examiner*—Brian J. Davis
*Attorney, Agent, or Firm*—Hale and Dorr LLP

[57] ABSTRACT

The invention is directed to therapeutically active hydroxamic acid derivatives of formula (I):

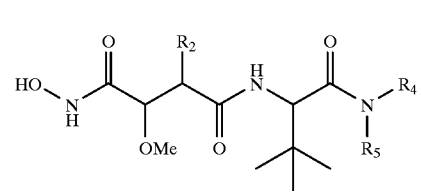

wherein the substituents are as defined in the specification. These therapeutically active hydroxamic acid derivatives have high intrinsic activity against a broad spectrum of matrix metalloproteinases (MMPs), good oral bioavailability, and additionally inhibit tissue necrosis factor (TNF) production.

11 Claims, No Drawings

MATRIX METALLOPROTEINASE INHIBITORS

The present invention relates to therapeutically active hydroxamic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND TO THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Metalloproteinases are characterised by the presence in the structure of a zinc(ll) ion at the active site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (L. M. Matrisian, *Trends in Genetics*, 1990, 6, 121–125).

Many known MMP inhibitors are peptide derivatives, based on naturally occurring amino acids, and are analogues of the cleavage site in the collagen molecule. Other known MMP inhibitors are less peptidic in structure, and may more properly be viewed as pseudopeptides or peptide mimetics. Such compounds usually have a functional group capable of binding to the active site zinc(ll) ion in the MMP, and known classes include those in which the zinc binding group is a hydroxamic acid, carboxylic acid, sulphydryl, and oxygenated phosphorus (eg phosphinic acid and phosphonic acid) groups.

A known class of pseudopeptide or peptide mimetic MMP inhibitors have a hydroxamic acid group as their zinc binding group. With a few exceptions, such known MMPs may be represented by the structural formula (IA)

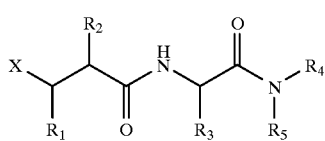

(IA)

in which X is the zinc binding hydroxamic acid (—CONHOH) group and the groups $R_1$ to $R_5$ are variable in accordance with the specific prior art disclosures of such compounds. The following patent publications disclose hydroxamic acid-based MMP inhibitors:

| | |
|---|---|
| US 4599361 | (Searle) |
| EP-A-231081 | (ICI) |
| EP-A-0236872 | (Roche) |
| EP-A-0274453 | (Bellon) |
| WO 90/05716 | (British Bio-technology) |
| WO 90/05719 | (British Bio-technology) |
| WO 91/02716 | (British Bio-technology) |
| WO 92/09563 | (Glycomed) |
| US 5183900 | (Glycomed) |
| US 5270326 | (Glycomed) |
| WO 92/17460 | (SmithKline Beecham) |
| EP-A-0489577 | (Celltech) |
| EP-A-0489579 | (Celltech) |
| EP-A-0497192 | (Roche) |
| US 5256657 | (Sterling Winthrop) |
| WO 92/13831 | (British Bio-technology) |
| WO 92/22523 | (Research Corporation Technologies) |
| WO 93/09090 | (Yamanouchi) |
| WO 93/09097 | (Sankyo) |
| WO 93/20047 | (British Bio-technology) |
| WO 93/24449 | (Celltech) |
| WO 93/24475 | (Celltech) |
| EP-A-0574758 | (Roche) |
| WO 94/02447 | (British Biotech) |
| WO 94/02446 | (British Biotech) |

The intrinsic potency of compounds within the broad structural groups of hydroxamic derivatives disclosed in the above publications against particular MMPs can be high. For example, many have a collagenase $IC_{50}$ by the in vitro test method of Cawston and Barrett, (Anal. Biochem., 99, 340–345, 1979) of less than 50 nM. Also, compounds are known which have high broad spectum intrinsic activities against the main MMP groups, namely the collagenases, gelatinases, stromelysins and PUMP. Unfortunately however, compounds known from these publications having high intrinsic in vitro inhibitory activity against one or more of the MMP targets often, indeed usually, have poor physicochemical and/or pharmacokinetic properties, rendering them of little value for oral administration, which of course is the preferred mode of administration in all but the most acute conditions for which MMP inhibitors are indicated. Since the oral bioavailability of a given compound is not in general predictable, the identification, through synthesis and testing, of hydroxamic acid-based MMP inhibitors having a good balance of high intrinsic activity against each of the three main classes of MMPs, namely the collagenases, the gelatinases and the stromelysins, and good physicochemical and/or pharmacokinetic properties, such that the compounds are easily formulated for administration, have good bioavailability for acceptable periods following oral administration, and have high in vivo activity in the target disease or condition, remains a much sought after goal in the art.

BRIEF DESCRIPTION OF THE INVENTION

This invention makes available a novel group of compounds of general formula (IA), principally characterised in that the $R_1$ substituent is methoxy, and $R_3$ is tert-butyl, in accordance with the invention it has been found that such compounds have the desirable characteristics of high intrinsic activity against a broad spectrum of MMPs, and good oral bioavailability, and additionally inhibit TNF production. Compositions containing compounds of the invention and adapted for oral administration to mammals, including farm mammals and human beings, are also part of the invention, as is a method for treating diseases or conditions mediated by MMPs and/or TNF by administering a compound of the invention orally.

The compounds of the invention are believed to be novel:

Of the patent publications listed above, it appears that only EP-A-0236872 refers to the possibility that in a particular class of collagenase inhibitors of basic structure (IA) the substituent $R_1$ may be alkoxy. That possibility is referred to amongst many other possible $R_1$ substituents, in the context of compounds in which the substituent $R_3$ is the characteristic side chain of a naturally occurring amino acid in which any functional substituents may be protected, any amino group may be acylated, and any carboxyl group may be esterified. That definition excludes the possibility that $R_3$ may be tert-butyl, as in the case of the compound of this invention. In any event, EP-A-0236872 does not disclose compounds in which $R_1$ is alkoxy as having preferred or particularly advantageous collagenase inhibitory properties, and in fact contains no disclosure of any specific compound in which $R_1$ is alkoxy. It does not address the problem in the art referred to above of providing hydroxamic acid derived MMP inhibitors having the elusive balance of good broad spectrum intrinsic activity profile and good physicochemical and/or pharmacokinetic properties, particularly oral bioavailability.

EP-A-0497192, and several other of the patent publications listed above disclose compounds conforming the formula (IA) above wherein $R_3$ is or may be tert-butyl, but neither EP-A-0497192 nor any of the other such publications allow the $R_1$ substituent to be methoxy, or indeed alkoxy.

WO 94/02447 discloses compounds of formula (IA) in which $R_1$ is hydroxy, and which are both highly active in vitro, and orally bioavailable. The compound of Example 10 of WO 94/02447 (known as BB-2516) is known to be a good example of the class disclosed therein. BB-2516 has a tert-butyl group at the position equivalent to $R_3$ in formula (IA). However, despite its good oral bioavailability and generally good broad spectrum activity profile, BB-2516 has only moderate in vitro activity against stromelysin.

WO 94/02447 does not itself disclose compounds of formula (IA) in which $R_1$ is alkoxy. However, the patent application GB 9215665.2, from which WO 94/02447 claims priority generically disclosed compounds having formula (IA) above in which $R_1$ is represents (inter alia) $(C_1-C_6)$alkoxy, $R_2$ represents (inter alia) $(C_1-C_6)$alkyl, $R^3$ represents (inter alia)$(C_1-C_6)$alkyl, $R_4$ represents $(C_1-C_6)$ alkyl and $R_5$ represents (inter alia) hydrogen. However, the preferred compounds of patent application GB 9215665.2 are stated to be those in which $R_1$ hydroxy. There is no specific disclosure of individual compounds failing within the broad generic disclosure other than the two specific examples, in which $R_1$ is hydroxy, namely the compounds of examples 1 and 2 of the WO 94/02447 publication.

DETAILED DESCRIPTION OF THE INVENTION

According to one aspect of the present invention, there is provided a compound of formula (I):

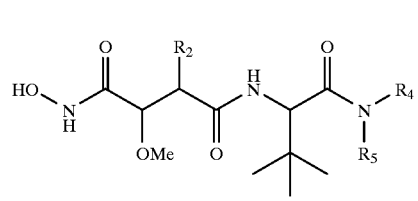

wherein
$R_2$ represents a group $R_6$-A- wherein A represents a divalent straight or branched, saturated or unsaturated hydrocarbon chain of up to 12 C atoms and $R_6$ represents hydrogen or an optionally substituted aryl, heterocyclyl, cycloalkyl or cycloalkenyl group; and
$R_4$ and $R_5$ each independently represents hydrogen, a $C_1-C_4$ alkyl group, or an aryl($C_1-C_4$ alkyl) group;
or a salt, solvate or hydrate thereof.

As used herein the term "$C_1-C_4$ alkyl" refers to a straight or branched chain alkyl moiety having from 1 to 4 carbon atoms, including for example, methyl, ethyl, n-propyl, iso-propyl, n-butyl, iso-butyl and t-butyl.

As used herein the term "saturated hydrocarbon chain of up to 12 C atoms" refers to a straight or branched chain alkyl moiety having from 1 to 12 carbon atoms, including for example, methyl, ethyl, propyl, isopropyl, butyl, t-butyl, n-pentyl, n-hexyl, n-septyl, n-octyl, n-nonyl, ndecyl, n-undecyl and n-dodecyl.

The term "unsaturated hydrocarbon chain of up to 12 C atoms" refers to a straight or branched chain alkenyl or alkynyl moiety having from 2 to 6 carbon atoms and having at least one alkynyl triple bond or one double bond of either E or Z stereochemistry. This term would include, for example, vinyl, 1-propenyl, 1- and 2-butenyl, 2-methyl-2-propenyl, 1-propynyl and 2-propynyl.

The term "aryl" refers to a mono-, bi- or tri-cyclic, substituted or unsubstituted carbocyclic aromatic group, and to groups consisting of two covalently linked substituted or unsubstituted monocyclic aromatic groups. Illustrative of such groups are phenyl, biphenyl, naphthyl and fluorenyl.

The term "cycloalkyl" refers to a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" refers to an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon at oms, the ring may contain more than one double bond.

The term "heterocyclyl" or "heterocyclic" refers to a 5–7 membered heterocyclic ring containing one or more heteroatoms selected from S, N and O, and optionally fused to a benzene ring, including for example, pyrolyl, furanyl, thienyl, imidazolyl, oxazolyl, thiazolyl, pyrazolyl, pyridinyl, pyrrolidinyl, pyrimidinyl, momholinyl, piperizinyl, indolyl and benzimidazole.

Unless otherwise specified in the context in which it occurs, the term "substituted" as applied to any moiety herein means substituted with up to four substituents, each of which independently may be $C_1-C_6$ alkoxy, hydroxy, thio, $C_1-C_6$ alkyithio, amino, halo (including fluoro, chloro, bromo and iodo), trifluoromethyl, nitro, cyano, phenyl, COOH, —$CONH_2$, —$CONHR^A$ or —$CONR^AR^A$ wherein $R^A$ is a $C_1-C_6$ alkyl group.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the methoxyoxy group and hydroxamic acid moiety —S,
C atom carrying the $R_2$ group —R.
C atom carrying the tert-butyl group —S, but mixtures in which the above configurations predominate are also contemplated.

In the compounds of the invention:

$R_2$ may for example be a $C_3$–$C_{12}$ alkyl, cycloalkyl($C_3$–$C_6$ alkyl), aryl($C_1$–C6 alkyl), aryl($C_2$–$C_6$ alkenyl) or aryl ($C_2$–$C_6$ alkynyl), any of which may be optionally substituted. Examples of particular $R_2$ groups include iso-butyl, n-hexyl, n-octyl,n-dodecyl, 3-cyclohexyipropyl, 4-cyclohexylbutyl, 5-cyclohexylpentyl, 2-phenylethyl, 3-phenylpropyl, 3-(4-chlorophenyl)-propyl, 3-(4-biphenyl)-propyl, 4-phenylbutyl, and 5-phenylpentyl.

$R_4$ and $R_5$ may for example both be methyl, or $R_4$ may be hydrogen while $R_5$ is methyl, ethyl, n-butyl, tert-butyl or benzyl.

Interesting compounds of the invention are:

$N^1$-(2,2-Dimethyl-1S-methylcarbamoyl-propyl)-$N^4$-hydroxy-2R-isobutyl-3S-methoxy-succinamide
$N^1$-(2,2-Dimethyl-1S-methylcarbamoyl-propyl)-$N^4$-hydroxy-3S-methoxy-2R-(3-phenylpropyl)-succinamide.
$N^1$-(2,2-Dimethyl-1S-methylcarbamoyl-propyl)-$N^4$-hydroxy-3S-methoxy-2R-(5-phenylpentyl)-succinamide.
$N^1$-(2,2-Dimethyl-1RS-butylcarbamoyl-propyl)-$N^4$-hydroxy-2R-isobutyl-3S-methoxy-succinamide
$N^1$-(2,2-Dimethyl-1RS-2,2-dimethylethylcarbamoyl-propyl)-$N^4$-hydroxy-2R-isobutyl-3S-methoxy-succinamide
$N^1$-(2,2-Dimethyl-1RS-benzylcarbamoyl-propyl)-$N^4$-hydroxy-2R-isobutyl-3S-methoxy-succinamide
$N^1$-(2,2-Dimethyl-1S-methylcarbamoyi-propyl)-2R-octyl-$N^4$-hydroxy-3S-methoxy-succinamide
$N^1$-(2,2-Dimethyi-1S-methylcarbamoyl-propyl)-2R-hexyl-$N^4$-hydroxy-3S-methoxy-succinamide
2R-(3-Biphenyl4-yl-propyl)-$N^1$-(2,2-dimethyl-1S-methylcarbamoyl-propyl)-$N^4$-hydroxy-3S-methoxy-succinamide
2R-(3-Biphenyl4-yl-prop-2-ynyl)-$N^1$-(2,2-dimethyl-1S-methylcarbamoyl-propyl)-$N^4$-hydroxy-3S-methoxy-succinamide
2R-[3-(4-Chlorophenyl)-propyl)]-$N^1$-(2,2-Dimethyl-1S-methylcarbamoyl-propyl)-$N^4$-hydroxy-3S-methoxy-succinamide
2R-[3-(4-Chlorophenyl)-prop-2-ynyl)]-$N^1$-(2,2-Dimethyl-1S-methylcarbamoyl-propyl)-$N^4$-hydroxy-3S-methoxy-succinamide
$N^1$-(1S-Dimethylcarbamoyl-2,2-dimethyl-propyl)-$N^4$-hydroxy-2R-isobutyl-3S-methoxy-succinamide and salts, solvates or hydrates thereof.

A compound of the invention which is presently especially preferred for its balance of high intrinsic activity in inhibiting MMPs, including stromelysin, and good pharmacokinetic properties, evidenced for example by high blood levels following oral administration, is:

$N^1$-(2,2-Dimethyl-1S-methylcarbamoyl-propyl)-$N^4$-hydroxy-2R-isobutyl-3S-methoxy-succinamide
and salts, solvates or hydrates thereof.

Compounds according to the present invention may be prepared by methods known per se in the art, and by the following process, which forms another aspect of the invention, namely a process for the preparation of a compound of formula (I) comprising:

(a) causing an acid of general formula (II

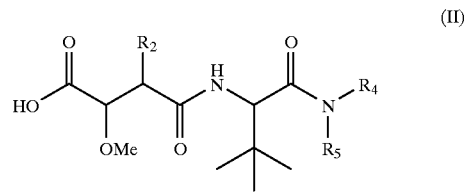

(II)

or an activated derivative thereof to react with hydroxylamine, O-protected hydroxylamine, or an N,O-diprotected hydroxylamine, or a salt thereof, $R_2$, $R_4$, and $R_5$ being as defined in general formula (I) except that any substituents in $R_2$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

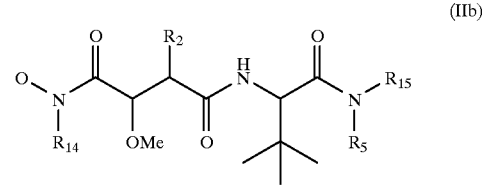

(IIb)

in which $R_2$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl carbodiimide (DCC), N,N-dimethylaminopropyl-'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

A compound of general formula (II) can be prepared by coupling an acid of formula (III) or an activated derivative thereof with an amine of formula (IV)

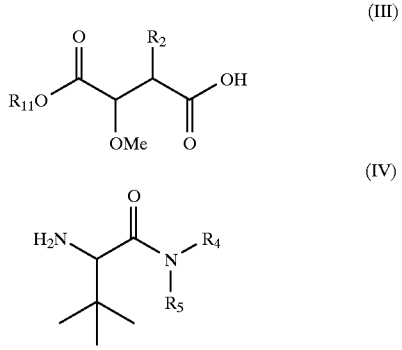

wherein $R_2$, $R_4$ and $R_5$ are as defined in general formula (I) and $R_{11}$, represents a carboxylic acid protecting group. Active derivatives of acids (III) include activated esters such as the pentafluorophenyl ester, acid anhydrides and acid halides, eg chlorides. Subsequent removal of the carboxylic acid protecting group $R_{11}$ provides the compound of general formula (II).

A compound of general formula (IIb) can be prepared by coupling an acid of formula (V) with an amine of formula (IV)

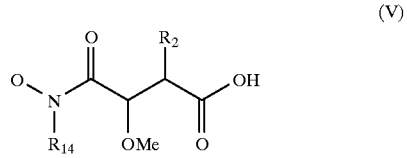

wherein $R_2$, $R_3$ and $R_5$ are as defined in general formula (I), $R_{14}$ is an amino protecting group and $R_{15}$ is a hydroxyl protecting group in the presence of a suitable coupling reagent (e.g. DCC).

Alternatively compounds of general formula (II and IIb) in which $R_4$ is hydrogen can be prepared by a Ugi condensation reaction between an acid of formula (III) or of general formula (V), an imine of formula (VII) and an isonitrile of formula (VIII)

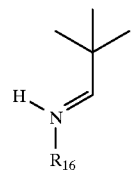

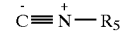

wherein $R_5$ is as defined in general formula (I) and $R_{16}$ is either hydrogen or an amino protecting group. This multi-component co-condensation method may be conducted in a protic solvent such as methanol or 2,2,2-trifluoroethanol, in an aprotic solvent (e.g. tetrahydrofuran, chloroform, methylene chloride or acetonitrile) or in a mixed protic/aprotic solvent system. Methanol is the presently preferred reaction medium, but selection of appropriate organic liquid media for specific combinations of reaction components is a matter of routine. The reaction components are added to the chosen liquid reaction medium and caused to co-react. In a modification of this method the imine is formed in situ by the reaction of trimethylacetaldehyde with a primary amine of formula (IX)

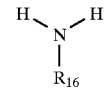

wherein $R_{16}$ is either hydrogen or an amino protecting group and the the other reagents the acid of general formula (IV) or (V) and the isonitrile of formula (VII) are then added either simultaneously or subsequently. In the case where the starting carboxylic acid is of general formula (III) subsequent removal of the carboxylic acid protecting group $R_{11}$ provides the compound of general formula (II). In the case where the $R_{16}$ group is an amino protecting group subsequent removal of this group is required.

Compounds of formula (III), (IV), (V), (VII), (Vil), (IX), are either known in the art or may be prepared by methods analogous to those used for the corresponding starting materials in the Examples below.

As used herein the term "amino protecting group" means a group which may be used for the protection, i.e. temporary blocking, of amino nitrogen functionality. Such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of amino protecting groups include allyl and benzyl or benzyl optionally substituted in the phenyl ring by one or more nitro or methoxy substituents, for example 4-methoxybenzyl or 2,4-dimethoxybenzyl.

As used herein the term "carboxylic acid protecting group" means a group which may be used for the protection, i.e. temporary blocking, of the oxygen functionality within a carboxylic acid. Again such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of carboxyl protecting groups include allyl, t-butyl, and benzyl or benzyi optionally substituted in the phenyl ring by one or more nitro or methoxy substituents, for example 4-methoxybenzyl or 2,4-dimethoxybenzyl.

As used herein the term "hydroxyl protecting group" means a group which may be used for the protection, i.e. temporary blocking, of the oxygen functionality of the hydroxyl group. Again such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of hydroxyl protecting groups include allyl, t-butyl, trimethylsilyl and benzyl or benzyl optionally substituted in the phenyl ring by one or more nitro or methoxy substituents, for example 4-methoxybenzyl or 2,4-dimethoxybenzyl.

Removal of amine protecting groups, carboxyl protecting groups or hydroxyl protecting groups as referred to above is a common procedure requiring little or no elaboration. The art of peptide synthesis is a prolific source of detailed knowledge of these methods, as is the reference work cited earlier, namely T. W. Greene and P. G. M. Wuts, Protective Groups in Organic Synthesis, 2nd Edition, Wiley, New York, 1991.

As mentioned above, compounds of formula (I) are useful in human or veterinary medicine since they are active as inhibitors of MMPs, and a further advantage lies in their ability to inhibit the release of tumour necrosis factor (TNF) from cells. Furthermore, they have a good balance of high intrinsic activity against MMPs, and good bioavailability after oral administration. In the latter respect, the methoxy compounds of the invention appear superior to their higher alkoxy homologues.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) or a salt, solvate or hydrate thereof for use in human or veterinary medicine, particularly in the management (by which is meant treatment or prophylaxis) of diseases or conditions mediated by MMPs and/or TNF; and (iii) the use of a compound as defined with respect to formula (I) or a salt, solvate or hydrate thereof in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration, tumour invasion by secondary metastases, multiple sclerosis, and angiogenesis dependent diseases, which include arthritic conditions and solid tumour growth as well as psoriasis, proliferative retinopathies, neovascular glaucoma, ocular tumours, angiofibromas and hemangiomas. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) or a salt, solvate or hydrate thereof together with a pharmaceutically or veterinarily acceptable excipient or carrier. In view of the water-solubility, and oral bioavailability advantanges of compounds in accordance with the invention, a further aspect of the invention comprises a pharmaceutical or veterinary composition comprising a compound of formula (I) or a salt, solvate or hydrate thereof together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl- pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embodiments of the invention:

The example which follows serves to illustrate the preparation of the compound the invention but is not intended to limit the scope in any way. Preparation of the starting material 2R-(2,2-dimethyl-5-oxo-[1,3]-dioxalan4S-yl)-4-methyl-pentanoic acid was described in WO 94/02447. 3,3-Dimethyl-5S-[2(RS)-cinnamyl]ethanoic acid-2,4-dioxalone was prepared by an analogous procedure starting from cinnamyl bromide instead of methallyl iodide.

The following abbreviations have been used throughout:

| | |
|---|---|
| DMF | N,N-Dimethylformamide |
| EDC | N-Ethyl-N'-(3-dimethylaminopropyl)carbodiimide hydrochloride |
| HOBt | 1-Hydroxybenzotriazole |
| NMM | N-Methylmorpholine |
| THF | Tetrahydrofuran |

$^1$H and $^{13}$C NMR sp ectra were recorded using a Bruker AC 250E spectrometer at 250.1 and 62.9 MHz, respectively. Elemental microanalyses were performed by MEDAC Ltd, Department of Chemistry, Brunel University, Uxbridge, Middlesex, UB8 3PH.

EXAMPLE 1

$N^1$-(2,2-Dimethyl-1S-methylcarbamoyl-propyl)-$N^4$-hydroxy-2R-isobutyl-3S-methoxy-succinamide

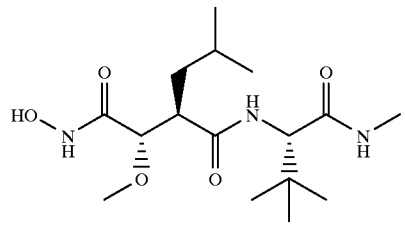

STEP A

2S-Hydroxy-3R-isobutyl-succinic acid dimethyl ester 2R-(2,2-Dimethyl-5-oxo-[1,3]-dioxalan-4S-yl)-4-methyl-pentanoic acid (75.0 g, 0.326 mol) was dissolved in methanol (500 ml) and cooled to 0° C. and the resulting solution was saturated with hydrogen chloride gas. The reaction mixture was allowed to warm to room temperature and stirred overnight. The solvent was removed under reduced pressure and the residue was dissolved in dichloromethane and washed successively with saturated sodium hydrogen carbonate and brine. The organic layer was dried (anhydrous magnesium sulphate), filtered and evaporated to dryness under reduced pressure to give the title compound (53 g, 75%). $^1$H-NMR; δ(CDCl$_3$), 4.10 (1H, d, J=4.0 Hz), 3.60 (3H, s), 3.50 (3H, s), 2.82–2.74 (1H, m), 1.61–1.40 (2H, m) 1.33–1.23 (1H, m) and 0.76–0.73 (6H, m).

STEP B 2R-lsobutyl-3S-methoxy-succinic acid dimethyl ester

2S-Hydroxy-3R-isobutyl-succinic acid dimethyl ester (9.6 g 44 mmol) was dissolved in DMF (5 ml) and distilled iodomethane (3.3 ml) and silver (I) oxide (11.2 g) were added. The reaction was stirred with the exclusion of light for 2 days at room temperature. The solvent was removed under reduced pressure and the residue was purified by column chromatography (silica gel, dichloromethane) to give the title compound as a yellow viscous liquid, 4.70 g (46%). $^1$H-NMR; δ(CDCl$_3$), 3.83 (1H, d, J=7.5 Hz), 3.71 (3H, s), 3.62 (3H, s), 3.30 (3H, s), 2.89–2.80 (1H, m), 1.65–1.39 (2H, m) 1.15–1.04 (1H, m) and 0.83–0.81 (6H, m).

STEP C 2R-lsobutyl-3S-methoxy-succinic acid dilithium salt

Lithium hydroxide (1.76 g, 42.0 mmol) was added to a solution of 2R-isobutyl-3S-methoxy-succinic acid dimethyl ester (4.70 g, 20.0 mmol) in methanol (30 ml) and water (30 ml). The reaction mixture was stirred at room temperature for 2 hours then solvents were removed under reduced pressure to give the product as a yellow solid (4.40 g, 100%). $^1$H-NMR; δ(CD$_3$OD), 3.52 (1H, d, J=5.1 Hz), 3.27 (3H, s), 2.69 –2.61 (1H, m), 1.56–1.53 (2H, m), 1.34–1.28 (1H, m) and 0.82–0.78 (6H, m).

STEP D

2R-Isobutyl-3S-methoxy-succinic acid 4-methyl ester 2R-lsobutyl-3S-methoxy-succinic acid dilithium salt (4.40 g, 20.0 mmol) was dissolved in THF (30 ml), the solution was cooled to 0° C. and trifluoroacetic anhydride (30 ml) was added. The reaction was stirred for 4 hours, the solvent was removed under reduced pressure and the residue was dissolved in methanol (2 ml) at 0° C. and stirred to room temperature overnight. The solvent was removed under reduced pressure to give the title compound as a yellow oil (7.0 g, including residual solvent), which was used without further purification in Step E. $^1$H-NMR; δ(CD$_3$OD ), 7.61 (1 H, d, J=7.5 Hz), 3.65 (3H, s), 3.24 (3H, s), 2.78–2.67 (1H, m), 1.56–1.42 (2H, m), 1.09–1.03 (1H, m) and 0.81–0.79 (6H, m).

STEP E 3R-(2,2-Dimethyl-1S-methylcarbamoyl-propylcarbamoyl)-2S-methoxy-5-methyl-hexanoic acid methyl ester 2R-lsobutyl-3S-methoxy-succinic acid 4-methyl ester (4.40 g, 20.0 mmol) was dissolved in DMF (50 ml) and EDC and HOBt were added. The solution was stirred for 2 hours at room temperature. L-tert-Leucine-N-methylamide (3.5 g, 24.0 mmol) was added and the reaction mixture was stirred at room temperature overnight. The solvent was removed under reduced pressure and the residue was dissolved in dichloromethane and washed successively with 1M hydrochloric acid, saturated sodium hydrogen carbonate and brine. The organic phase was dried (anhydrous magnesium sulphate), filtered and evaporated to leave a yellow gum which was purified by column chromatography (silica gel, gradient elution, 3 to 4% methanol in dichloromethane) to give the title compound as a yellow foam (4.30 g, 62%). $^1$H-NMR; δ(CDCl$_3$), 7.35 (1H, m), 6.75 (1H, d, J=9.4 Hz), 4.33 (1H, d, J=9.4 Hz), 3.71 (1H, d, J=7.7 Hz), 3.61 (3H, s), 3.21 (3H, s), 3.19–2.56 (4H, m), 1.53–1.29 (2H, m), 1.02–0.92 (1H, m), 0.85 (9H, s) and 0.71–0.69 (6H, m).

STEP F

3R-(2,2-Dimethyl-1S-methylcarbamoyl-propylcarbamoyl)-2S-methoxy-5-methyl-hexanoic acid Lithium hydroxide (550 mg, 13.0 mmol) was added to a solution of 3R-(2,2-dimethyl-1S-methylcarbamoyi-propylcarbamoyl)-2S-methoxy-5-methyl-hexanoic acid methyl ester (4.30 g, 12.0 mmol) in methanol (40 ml) and water (40 ml) and the reaction mixture was stirred at room temperature overnight. The solvents were removed under reduced pressure to give a pale yellow foam which was dissolved in ethyl acetate and washed with 1M hydrochloric acid. The organic phase was dried (anhydrous magnesium sulphate) and concentrated under reduced pressure to give the product as an off-white solid, 3.70 g (93%). $^1$H-NMR; $\delta$(CDCl$_3$/CD$_3$OD), 4.01 (1H, s), 3.51 (1H d, J=6.5 Hz), 3.24 (3H, s), 3.22–3.18 (1H, m), 2.61 (3H, s), 1.58–1.39(2H, m), 1.37–1.20 (1H, m), 0.91 (9H, s) and 0.81–0.76 (6H, m).

STEP G

N$^1$-(2,2-Dimethyl-1S-methylcarbamoyl-propyl)-N$^4$-hydroxy-2R-isobutyl-3S-methoxy-succinamide To a stirred solution of 3R-(2,2-dimethyl-1S-methylcarbamoyl-propylcarbamoyl)-2S-methoxy-5-methyl-hexanoic acid (3.70 g, 11.0 mmol) in DMF (40 ml), EDC (1.80 g, 13.0 mmol) and HOBt (3.20 g, 17.0 mmol) were added. The reaction was stirred for 5 hours. In a separate vessel, NMM (2.6 ml, 22.0 mmol) was added to a stirred solution of hydroxylamine hydrochloride (2.30 g, 33.0 mmol) in DMF (10 ml), thus liberating free base, and this was added with stirring to the previous reaction mixture. The reaction was allowed to proceed at room temperature overnight, after which the solvent was removed under reduced pressure and the residue triturated with ether/water (2:1). The precipitated white solid (HOBt) was removed by filtration and the filtrate was concentrated under reduced pressure then purified by column chromatography (acid-washed silica, eluent 5% methanol in dichloromethane). The resulting white solid was further purified by slurrying with ethyl acetate and filtration to afford the tite compound 420 mg ( 11%). $^1$H-NMR; $\delta$(CD$_3$OD), 4.17 (1H, s), 3.47 (1H, d, J=9.3 Hz), 3.16 (3H, s), 2.77–2.67 (1H, m), 2.61 (3H, s), 1.52–1.27 (2H, m), 1.06–0.89 (10H, m) and 0.79–0.73 (6H, m). $^{13}$C-NMR; $\delta$(MeOD), 174.9, 173.1, 169.5, 83.0, 62.2, 58.2, 49.2, 38.5, 35.5, 27.1, 26.0, 24.0 and 22.0. IR (KBr) $v_{max}$, 3312, 2958, 2396, 1662, 1543, 1468, 1398, 1369, 1259, 1222, 1111, 1019, 966, 936, 814, 750, 640 cm$^{-1}$. Found: C 54.80, H 9.06, N 11.93%; C$_{16}$H$_{31}$N$_3$O$_5$. 0.3H$_2$O requires C 54.77, H 9.08, N 11.98%.

EXAMPLE 2

N$^1$-(2,2-Dimethyl-1S-methylcarbamoyl-propyl)-N$^4$-hydroxy-3S-methoxy-2R-(3-phenylpropyl)-succinamide

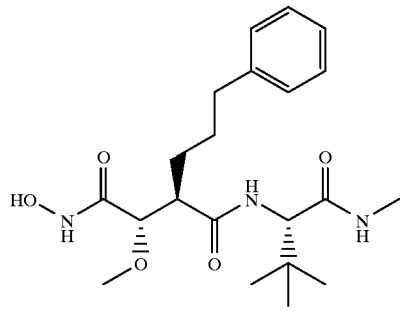

STEP A

3S-Hydroxy-2RS-(3-phenylallyl)-succinic acid dimethyl ester 3,3-Dimethyl-5S-[2RS-cinnamyl]ethanoic acid-2,4-dioxalone (6:1 mixture of diastereoisomers; 22.66 g, 78 mmol) was transformed by the method described as Example 1 (Step A) to give the title compound as a brown oil (mixture of diastereoisomers, 22.20 g, including residual solvent), which was used without further purification in Step B. $^1$H NMR; $\delta$(CDCl$_3$), 7.30 (5H, m), 6.55 (1H, d, J=15.8 Hz), 6.10–6.30 (1H, m), 4.60–4.36 (1H, br m), 3.80 (3H, s), 3.70 (3H, s), 3.20 (1H, br s), 3.10 (1H, m), 2.88–2.59 (2H, m).

STEP B

3S-Methoxy-2RS-(3-phenylallyl)-succinic acid dimethyl ester

3S-Hydroxy-2RS-(3-phenylallyl)-succinic acid dimethyl ester (22.2 g, 80.0 mmol) was O-alkylated by the method described in Example 1 (Step B). Purification by column chromatography (silica gel, dichloromethane) gave the title compound as a yellow solid (2.95 g as a single diastereomer, 6.77 g as a mixture of diastereomers, 42% overall). $^1$H NMR; $\delta$(CDCl$_3$, single diastereoisomer), 7.30 (5H, m), 6.48 (1H, d, J=5.7 Hz), 6.16 (1H, m), 4.98 1H, d, J=6.0 Hz), 3.78 (3H, s), 3.69 (3H, s), 3.43 (3H, s), 3.05 (1H, m), 2.68–2.43 (2H, m).

STEP C

3S-Methoxy-2RS-(3-phenylpropyl)-succinic acid dimethyl ester

3S-Methoxy-2RS-(3-phenylallyl)-succinic acid dimethyl ester (6.77 g, 23.2 mmol) was dissolved in methanol (100 ml) and ethyl acetate (10 ml) and resulting solution was placed under a blanket of argon. Pd-C catalyst (677 mg) was added and resulting mixture hydrogenated at atmospheric pressure and room temperature overnight. The system was purged with argon and the catalyst was removed by filtration. The filtrate was concentrated under reduced pressure to give the title compound as a yellow oil (mixture of diastereomers, 5.66 g, 83%). $^1$H NMR; $\delta$(CDCl$_3$), 7.31 (5H, m), 4.05–3.94 (1H, m), 3.75 (3H, s), 3.71 (3H, s), 3.42 (1H, s), 3.38 (2H, s), 2.85 (1H, m), 2.61 (2H, t, J=7.0 Hz), 1.70–1.61 (4H, m).

STEP D

3S-Methoxy-2RS-(3-phenylpropyl)-succinic acid

3S-Methoxy-2RS-(3-phenylpropyl)-succinic acid dimethyl ester (2.04 g, 7.3 mmol) was taken up in 1,4-dioxane (20 ml) and water (20 ml) was added with stirring followed by a 20% aqueous potassium hydroxide solution. The reaction mixture was stirred at room temperature for 4 hours, then heated at 90° C. overnight. After cooling to room temperature the reaction mixture was acidified with 1M hydrochloric acid and concentrated under reduced pressure. The resulting residue was extracted repeatedly with ethyl acetate and the combined extracts were dried and evaporated to dryness to give a yellow oil (mixture of diastereomers, 1.89 g, 97%). $^1$H NMR; $\delta$(CDCl$_3$), 7.31 (5H, m), 4.03–3.94 (1H, m), 3.48 (3H, s), 2.99 (1H, m), 2.66 (2H, t, J=7.0 Hz), 1.91–1.67 (4H, m).
STEP E 3S-Methoxy-2R-(3-phenyl-propyl)-succinic acid 4-methyl ester 3S-Methoxy-2R-(3-phenylpropyl)-succinic acid (1.89 g, 7.1 mmol) was transformed by the method detailed as Example 1 (Step D) to give the title compound as a dark yellow oil (mixture of diastereomers, 2.75 g, including residual solvent), which was used without further purification in Step E. $^1$H NMR; $\delta$(CDCl$_3$), 7.31 (5H, m), 5.80 (1H, br s), 4.11–3.96 (1H, m), 3.75, 3.50 (3H, 2s), 3.44, 3.41 (3H, 2s), 2.88 (1H, m), 2.63 (2H, t, J=7.0 Hz), 1.90–1.52 (4H, m).
STEP F 3R-(2,2-Dimethyl-1S-Methylcarbamoyl)-2S-methoxy-6-phenyl-1-hexanoic acid methyl ester 3S-Methoxy-2R-(3-phenylpropyl)-succinic acid 4-methyl ester (2.75 g) was dissolved in ethyl acetate (50 ml) and HOBt (959 mg, 7.1 mmol) was added with stirring, followed by EDC (1.36 g, 7.1 mmol) and L-tert-leucine-N-methyl amide (1.02 g, 7.1 mmol). The resulting mixture was heated at reflux for 4½ hours and then cooled to room temperature and diluted with ethyl acetate (50 ml). The solution was washed successively with water, 1M hydrochloric acid, water, saturated sodium hydrogen carbonate and brine, then dried over anhydrous magnesium sulphate. The solvent was removed under reduced pressure to yield a dark yellow gum which was purified by column chromatography silica gel, ethyl acetate) to give the title compound as a foam (1.33 g, 46%). $^1$H NMR; $\delta$(CDCl$_3$), 7.30 (5H, m), 6.69 (1H, d, J=9.4 Hz), 6.15 (1H, br m), 4.15 (1H, d, J=9.0 Hz), 3.89 (1H, d, J=6.6 Hz), 3.75 (3H, s), 3.40 (3H, s), 2.78 (3H, d, J=4.7 Hz), 2.62 (2H, t, J=7.5 Hz), 1.90–1.59 (4H, m) and 1.00 (9H, s).
STEP G 3RS-(2,2-Dimethyl-1S-Methylcarbamoyl-propylcarbamoyl)-2S-methoxy-6-phenyl 1-hexanoic acid 3RS-(2,2-Dimethyl-1S-methylcarbamoyl)-2S-methoxy-6-phenyl 1-hexanoic acid methyl ester (1.00 g, 2.46 mmol) was saponified using the method described in Example 1 (Step F), to give the title carboxylic acid as a white solid (mixture of diastereoisomers; 780 mg, 77%). $^1$H NMR; $\delta$(CD$_3$OD), 7.11 (5H, m), 4.16–4.09 (1H, m), 3.82–3.69 (1H, m), 3.31, 3.21 (3H, 2s), 2.70 (1H, m), 2.61, 2.56 (3H, 2s), 2.50–2.44 (2H, m), 1.56–1.39 (4H, m) and 0.88 (9H, s). $^{13}$C NMR; $\delta$(CD$_3$OD, major diastereoisomer), 177.1, 177.0, 175.5, 145.7, 131.8, 131.7, 129.2, 85.7, 64.6, 61.1, 53.1, 38.9, 37.9, 32.4, 31.7, 29.5 and 28.4. IR (KBr)v$_{max}$, 3303, 2955, 1716, 1634, 1544, 1456, 1409, 1367, 1265, 1114, 748 and 699 cm$^{-1}$.
STEP H N$^1$-(2,2-Dimethyl-1S-methylcarbamoyl-propyl)-N$^4$-hydroxy-3S-methoxy-2R-(3-phenylpropyl)-succinamide 3RS-(2,2-Dimethyl-1S-methylcarbamoyl-propylcarbamoyl)-2S-methoxy-6-phenyl-1-hexanoic acid (3.79 g, 9.70 mmol) was taken up in freshly distilled THF and cooled to –20° C. under Ar. Isobutyl chloroformate (1.9 ml, 14.6 mmol) and NMM (1.6 ml, 14.6 mmol) were added and the resulting mixture stirred for 20 minutes. O-(Trimethylsilyl)-hydroxyiamine (1.5 ml, 14.6 mmol) was then added and after a further 2 hours at –20 ° C. the reaction was warmed to room temperature. The precipitated solid was filtered off and the filtrate was concentrated under reduced pressure. The resulting yellow oil was purified by column chromatography (acid washed silica gel, 5% methanol in dichloromethane) to give the product as a pale yellow foam (mixture of diastereoisomers). $^1$H NMR; $\delta$(CD$_3$OD), 7.10 (5H, m), 4.18–4.05 (1H, m), 3.68–3.53 (1H, m), 3.24, 3.15 (3H, 2s), 2.70 (1H, m), 2.61, 2.56 (3H, 2s), 2.50–2.30 (2H, m), 1.60–1.20 (4H, m) and 0.89 (9H, s). $^{13}$C NMR; $\delta$(CD$_3$OD, major diastereoisomer), 177.2, 175.6, 171.8, 145.8, 131.8, 131.7, 129.2, 85.1, 64.6, 60.6, 53.1, 39.0, 37.9, 32.6, 31.6, 29.5 and 28.5. IR (KBr)v$_{max}$, 3292, 2956, 1656, 1540, 1454, 1369, 1237, 1107, 1030, 952, 749 and 699 cm$^{-1}$. Found: C 59.62, H 7.91, N 9.86%; C$_{21}$H$_{33}$N$_3$O$_5$. 0.9H$_2$O requires C 59.53, H 8.28, N 9.92%.

EXAMPLE 3

N$^1$-(2,2-Dimethyl-1S-methyicarbamoyl-propyl)-N$^4$-hydroxy-3S-methoxy-2R-(5-phenylpentyl)-succinamide

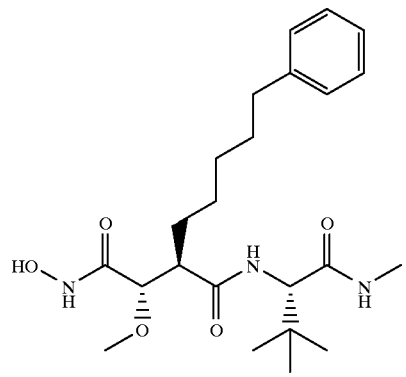

STEP A

Trifluoro-methanesulphonic acid 5-phenylpentyl ester

5-Phenyl-pentan-1-ol (2 g, 12.17 mmol) in dichloromethane (30 ml) was cooled to –78° C. and treated sequentially with trifluoro-methanesulphonic anhydride (2.25 ml, 13.39 mmol) and pyridine (1.08 ml, 13.39 mmol). The solution was then allowed to warm to 0°C. and stirred at 0° C. for 1 hour, when it was poured into water (30 ml) and the phases separated. The organic phase was dried over anhydrous magnesium sulphate, filtered through a short silica pad and concentrated in vacuo to provide the crude product as a colourless oil which was used directly in the next step. $^1$H-NMR; $\delta$(CDCl$_3$), 7.22 (5H, m), 4.55 (2H, dd, J=6.5 Hz), 2.66 (2H, dd, J=7.4 Hz), 1.89 (2H, m), 1.71 (2H, m) and 1.49 (2H, m).
STEP B 3S-Hydroxy-2R-(5-phenylpentyl)-succinic acid dimethyl ester A solution of di-isopropyl amine (3.05 ml, 23.23 mmol) in THF (20 ml) was cooled to 0° C. and treated with n-butyl lithium (23.23 mmol, 2 M solution in hexanes). The solution was stirred at 0° C. for 30 minutes when a solution of di-methyl-S-malate (1.45 ml, 11.06 mmol) in THF (10 ml) was added. The resulting solution was stirred at 0° C. for 1 hour then cooled to −78° C. and treated with a solution of the crude trifluoro-methanesulphonic acid 5-phenyl-pentyl ester in anhydrous toluene (20 ml) and stirred at −5° C. for 2 hours. The reaction was quenched with a saturated ammonium chloride solution (30 ml), poured into diethyl ether (30 ml) and the phases separated. The aqueous phase was extracted with ethyl acetate (30 ml). The organic phases combined, washed with 1 M hydrochloric acid (2×25 ml), saturated sodium hydrogen carbonate (25 ml) and brine (25 ml), dried over anhydrous magnesium sulphate, filtered and concentrated in vacuo. The resulting brown oil was purified by column chromatography (silica gel, 40% ethyl acetate in hexane) to provide the title compound as a colourless oil (1.04 g, 3.37 mmol, 30%, 4:1 mixture of diastereomers by $^1$H-NMR). $^1$H-NMR; $\delta$(CDCl$_3$, major diastereoisomer), 7.19 (5H, m), 4.28 (1H, dd, J=3.7, 6.7 Hz), 3.79 (3H, s), 3.68 (3H, s), 3.23 (1H, d, J=7.5 Hz), 2.86 (1H, ddd, J=11.0, 7.3 and 3.8 Hz), 2.61 (2H, dd, J=4.7 Hz), 1.83 (1H, m, 1.64 (3H, m) and 1.39 (4H, m).

STEP C

3S-Methoxy-2R-(5-phenylpentyl)-succinic acid dimethyl ester

The title compound was prepared according to the procedure outlined in Example 1 (Step B). Purification of the resulting yellow oil by column chromatography (silica gel, 20% ethyl acetate in hexane) provided product as a colourless oil (64%). $^1$H-NMR; $\delta$(CDCl$_3$), 7.18 (5H, m), 3.93, (1H, d, J=7.6 Hz), 3.78 (3H, s), 3.71 (3H, s), 3.38 (3H, s), 2.81 (1 H, s), 2.59 (2H, dd, J=7.5 Hz), 1.61 (3H, m) and 1.33 (5H, m).

STEP D

3S-Methoxy-2R-(5-phenylpentyl)-succinic acid

Lithium hydroxide (192 mg, 4.56 mmol) was added to a solution of 3S-methoxy-2R -(5-phenyl-pentyl)-succinic acid dimethyl ester (0.7 g, 2.17 mmol) in methanol (5 ml) and water (2 ml). The reaction mixture was stirred at room temperature for 2 hours then solvents were removed under reduced pressure to give a yellow solid which was dissolved in water (5 ml) and acidified to pH 2 with 1 M hydrochloric acid. The solution was extracted with ethyt acetate (3×20 ml) and the organic phase was dried over anhydrous magnesium sulphate, filtered and concentrated in vacuo to a colourless gum which was dried under reduced pressure to provide the title compound as a white solid (0.52g, 1.77 ml. 81%). $^1$H-NMR; $\delta$(CD$_3$OD), 7.10 (5H, m), 4.82 (2H, br s), 3.98 (1H, d, J=7.1 Hz). 3.25 (3H, s), 2.60 (1H, m), 2.48 (2H, dd, J=7.5 Hz), 1.49 |(4H, m) and 1.25 (4H, m).

STEP E

3S-Methoxy-2R-(5-phenylpentyl)-succinic anhydride

A solution of 3S-methoxy-2R-(5-phenyl-pentyl)-succinic acid (0.52 g, 1.77 mmol) in THF (10 ml) was cooled to 0° C. and treated dropwise with trifluoro-acetic anhydride (0.31 ml, 2.21 mmol). The solution was stirred at 0° C. for 4 hours when solvents were removed under reduced pressure, azeotroping with toluene. The residue was dissolved in diethyl ether (20 ml) and washed successively with water, saturated sodium hydrogen carbonate and brine (10 ml), dried over anhydrous magnesium sulphate, filtered and concentrated to an orange oil (0.3 g, 1.09 mmol, 61%). $^1$H-NMR; $\delta$(CDCl$_3$), 7.22 (5H, m), 4.25 (1H, d, J=7.5 Hz), 3.62 (3H, s), 3.08 (1H, dd, J=14.3 and 7.5 Hz), 2.63 (2H, dd, J=7.4 HZ), 1.80 (1H, m), 1.66 (3H, m) and 1.41 (4H, m)

STEP F 2R-(S-Benzyloxycarbamoyl-methoxy-methyl)-7-phenyl-heptanoic acid

O-Benzyl hydroxylamine (141 mg, 1.15 mmol) was added to a solution of 3S-methoxy-2R-(5-phenyl-pentyl)-succinic anhydride (300 mg, 1.09 mmol) in ethyl acetate (5 ml) and the resulting solution stirred at ambient temperature for 1 hour. Solvent was evaporated under reduced presure to provide the title compound as a pale yellow oil (0.43 g, 1.07 mmol, 98%). $^1$H-NMR; $\delta$(CDCl$_3$), 8.95 (1H, br s), 7.38 (5H, m), 7.25 (5H, m), 4.94 (2H, dd, J=13.5 and 11.4 Hz), 3.91 (1H, d, j=5.9 Hz), 3.33 (3H, s), 2.77 (1H, m), 2.59 (2H, dd, J=7.6 Hz), 1.62 (4H, m) and 1.35 (4H, m).

STEP G

N$^4$-Benzyloxy-N$^1$-(2,2dimethyl-1-methylcarbamoyl-propyl)-3S-methoxy-2R-(5-phenylpentyl) -succinamide 2R-(S-Benzyloxycarbamoyl-methoxy-methyl)-7-phenyl-heptanoic acid (430 mg, 1.07 mmol) and L-tert-leucine-N-methyl amide (185 mg, 1.28 mmol) were dissolved in THF (20 ml) and cooled to 0° C. EDC (246 mg, 1.28 mmol) was added and the resulting solution was stirred at 0° C. for 1 hour then at ambient temperature overnight. Solvent was removed in vacuo and the residue dissolved in dichloromethane (30 ml) and washed sequentially with 1 M hydrochloric acid, saturated sodium hydrogen carbonate and brine (2×20 ml), dried over anhydrous magnesium sulphate, filtered and concentrated under reduced pressure. The product was purified by column chromatography (silica gel, 10% methanol in dichloromethane) to provide the title compound as a colourless glassy solid (250 mg, 0.47 mmol, 44%). $^1$H-NMR; $\delta$(CDCl$_3$), 9.83 (1H, s), 7.39 (5H, m), 7.24 (5H, m), 6.63 (1H, br s), 4.87 (2H, dd, J=10.8 and 21.4 Hz), 4.20 (1H, d, J=9.4 Hz), 3.78 (1H, d, J=4.2 Hz), 3.35 (3H, s), 2.74 (3H, d, J=4.8 Hz), 2.66 (1H, m), 2.57 (2H, dd, J=7.5 Hz), 1.71 (1H, m), 1.58 (3H, m), 1.32 (4H, m) and 0.98 (9H, s).

STEP H

N$^1$-(2,2-Dimethyl-1-methylcarbamoyl-propyl)-N$^4$-hydroxy-3S-methoxy-2R-(5-phenyl-pentyl)-succinamide A solution of N$^4$-benzyloxy-N$^1$-(2,2-dimethyl-1-methylcarbamoyl-propyl)-3S-methoxy-2R -(5-phenylpentyl)-succinamide (250 mg. 0.47 mmol) in methanol (20 ml) containing a suspension of 10% palladium on charcoal (50 mg) was stirred vigorously under an atmosphere of hydrogen gas for 2 hours. The catalyst was removed by filtration and solvent evaporated under reduced pressure to provide a white gum which was dried in vacuo. Trituration with diethyl ether then filtration provided the title compound as a white solid (141 mg, 0.32 mmol, 69%). m.p. 103–105° C. $^1$H-NMR; $\delta$(CD$_3$OD), 7.03 (5H, m), 4.19 (1H, s), 3.52 (1H, d, J=9.5 Hz), 3.15 (3H, s), 2.63 (1H, m), 2.59 (3H, s), 2.44 (2H, t, J=7.3 Hz), 1.45 (3H, m), 1.16 (5H, m), and 0.89 (9H, s). $^{13}$C -NMR; $\delta$(CD$_3$OD), 177.3, 175.6, 171.9, 146.3, 131.8, 131.6, 129.0, 85.1, 64.6, 60.5, 53.4, 39.0, 37.9, 34.7, 32.4, 31.8, 30.2, 29.8, 29.5 and 28.5. IR (KBr)$v_{max}$; 3305, 2936, 2863, 1640, 1535, 1456, 1366, 1103, 750 and 697 cm$^{-1}$. Found: C 62.24, H 8.30, N 9.34%; C$_{23}$H$_{37}$N$_3$O$_5$.0.5H$_2$O requires C 62.14, H 8.62, N 9.45%.

EXAMPLE 4

N$^1$-(2,2-Dimethyl-1RS-butylcarbamoyl-propyl)-N$^4$-hydroxy-2R-isobutyl-3S-methoxy-succinamide

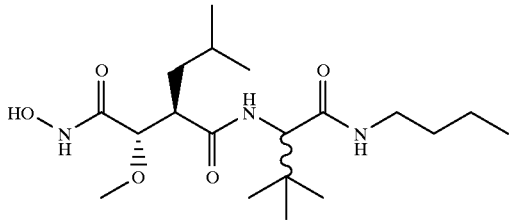

STEP A 2S-(S-Benzyloxycarbamoyl-methoxy-methyl)-4-methyl-pentanoic acid

The title compound was prepared by a method analogous to that described in Example 3 (Steps D, E and F), starting from 2R-isobutyl-3S-methoxy-succinic acid dimethyl ester (Example 1, Step B). $^1$H-NMR; $\delta$(CDCl$_3$), 9.03 (1H, br s), 8.72 (1H, br s), 7.39 (5H, m), 4.94 (2H, dd, J=11.4, 16.7 Hz), 3.92 (1H, dd, J=3.1 Hz), 3.33 (3H, s), 2.88 (1H, m), 1.65 (1H, m), 1.28 (2H, m) and 0.91 (6H, dd, J=4.4, 6.4 Hz).

STEP B

N$^4$Benzyloxy-N$^1$-(2,2-dimethyl-1RS-butylcarbamoyl-propyl)-2R-isobutyl-3S-methoxy-succinamide Trimethylacetaldehyde (0.065 ml, 0.6 mmol) was added at room temperature to a stirred 2 M solution of ammonia in methanol (0.6 ml, 1.2 mmol). After 30 min, a methanolic solution of 0.73 M n-butyl isocyanide (0.27 ml, 0.6 mmol) was added followed by a 0.58 M methanolic solution of 2R-(S-benzyloxycarbamoyi-methoxy-methyl) -4-methyl-pentanoic acid (1.0 ml, 0.6 mmol). The mixture was left to stand overnight and concentrated under reduced pressure to give the crude title compound as a white foam (361 mg) which was used in Step C without further purification. $^1$H NMR $\delta$(CDCl$_3$), 9.95–9.80 (1H, m), 8.35–8.20 (1H, m), 7.50–7.30 (5H, m) 6.70–6.40 (1H, m), 5.00–4.80 (2H, m), 4.25–4.15 (1H, m ), 3.40–2.70 (7H, m) and 1.90–0.79 (25H, m.)

STEP C

N$^1$-(2,2-Dimethyl-1RS-butylcarbamoyl-propyl)-N$^4$-hydroxy-2R-isobutyl-3S-methoxy-succinamide A mixture of crude N$^4$-benzyloxy-N$^1$-(2,2-dimethyl-1-butylcarbamoyl-propyl)-2R -isobutyl-3S-methoxy-succinamide (361 mg) and 10% palladium on carbon (54 mg) in methanol (40 ml) was stirred overnight at room temperature under an atmosphere of hydrogen. The mixture was filtered, concentrated under reduced pressure to give crude title compound as a yellow foam (235 mg, ca. quant. over steps B/C). $^1$H-NMR; (CD$_3$OD), 4.18 (0.5H, d, J=9.7 Hz), 4.12 (0.5H, d, J=9.2Hz), 3.44 (1H, br d, J=9.4 Hz), 3.16 (1.5H, s), 3.14 (1.5H, s), 3.12–3.00 (2H, m), 2.80–2.63 (1H, m) 1.61–1.19 (6H, m) and 0.98–0.73 (19H, m).

The following compounds were prepared by similar methods to those described in Example 4, substituting the appropriate isocyanides for n-butyl isocyanide:

EXAMPLE 5

N$^1$-(2,2-Dimethyl-1RS-2,2-dimethylethylcarbamoyl-propyl)-N$^4$-hydroxy-2R-isobutyl-3S-methoxy-succinamide

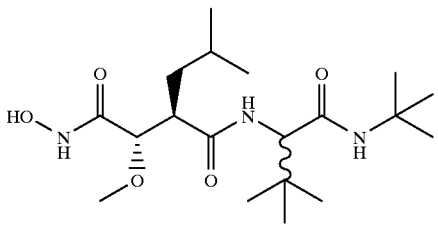

$^1$H-NMR; $\delta$(CD$_3$OD), 4.10 (1H, br d, J=11.5 Hz), 3.46 (1 H, br d, J=9.3 Hz), 3.16, 3.14 (3H, 2 s), 2.80–2.60 (1H, m), 1.60–1.10 (2H, m), 1.22, 1.21 (9H, 2s), 1.00–0.80 (1H, m), 0.90 (9H, s) and 0.85–0.70 (6H, m).

EXAMPLE 6

N$^1$-(2,2-Dimethyl-1RS-benzylcarbamoyl-propyl)-N$^4$-hydroxy-2R-isobutyl-3S-methoxy-succinamide

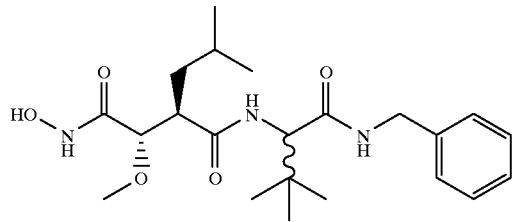

$^1$H-NMR; $\delta$(CD$_3$OD), 7.26–7.11 (5H, m), 4.34–4.18 (3H, m), 3.45 (0.5H, d, J=9.5 Hz), 3.42 (0.5H, d, J=9.5 Hz), 3.20 (1.5H, s), 3.15 (1.5H, s), 2.80–2.60 (1H, m), 1.60–1.20 (2H, m), 0.93 (4.5H, s), 0.90 (4.5H, s) and 1-00-0.60 (7H, m).

What is claimed is:

1. A compound of formula (I):

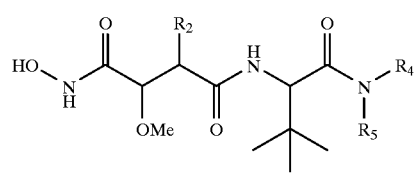

(I)

wherein

R$_2$ represents a group R$_6$—A— wherein A represents a divalent straight or branched, saturated or unsaturated hydrocarbon chain of up to 12 C atoms and R$_6$ represents hydrogen or an optionally substituted aryl, heterocyclyl, cycloalkyl or cycloalkenyl group; and R$_4$ and R$_5$ each independently represents hydrogen, a C$_1$–C$_4$ alkyl group, or an aryl(C$_1$–C$_4$ alkyl) group;

or a salt, solvate or hydrate thereof.

2. A compound as claimed in claim 1 wherein the stereochemistry is as follows:

C atom carrying the methoxy group and hydroxamic acid moiety —S,

C atom carrying the $R_2$ group —R,

C atom carrying the tert-butyl group —S.

3. A compound as claimed in claim 1 or claim 2 wherein $R_2$ represents a $C_3$–$C_{12}$ alkyl, cycloalkyl($C_3$–$C_6$ alkyl), aryl($C_1$–$C_6$ alkyl), aryl($C_2$–$C_6$ alkenyl) or aryl ($C_2$–$C_6$ alkynyl), any of which may be optionally substituted.

4. A compound as claimed in claim 3 wherein $R_2$ represents n-hexyl, n-octyl, n-dodecyl, 3-cyclohexylpropyl, 4-cyclohexylbutyl, 5-cyclohexylpentyl, 2-phenylethyl, 3-phenylpropyl, 3-(4-chlorophenyl)-propyl, 3-(4-biphenyl)-propyl, 4-phenylbutyl and 5-phenylpentyl.

5. A compound as claimed in claim 3 wherein $R_2$ represents isobutyl.

6. A compound as claimed in claim 3, wherein $R_4$ and $R_5$ are both methyl, or $R_4$ is hydrogen while $R_5$ is n-butyl, tert-butyl or benzyl.

7. A compound as claimed in claim 6 R4 is hydrogen while $R_5$ is methyl.

8. A compound selected from the group consisting of;

$N^1$-(2,2-Dimethyl-1S-methylcarbamoyl-propyl)-$N^4$-hydroxy-2R-isobutyl-3S-methoxy-succinamide $N^1$-(2,2-Dimethyl- 1S-methylcarbamoyl-propyl)-$N^4$-hydroxy-3S-methoxy-2R-(3-phenylpropyl)-succinamide $N^1$-(2,2-Dimethyl-1S-methylcarbamoyl-propyl)-$N^4$-hydroxy-3S-methoxy-2R-(5-phenylpentyl)-succinamide $N^1$-(2,2-Dimethyl-1RS-butylcarbamoyl-propyl)-$N^4$-hydroxy-2R-isobutyl-3S-methoxy-succinamide $N^1$-(2,2-Dimethyl-1RS-2,2-dimethylethylcarbamoyl-propyl)-$N^4$-hydroxy-2R-isobutyl-3S-methoxy-succinamide $N^1$-(2,2-Dimethyl-1RS-benzylcarbamoyl-propyl)-$N^4$-hydroxy-2R-isobutyl-3S-methoxy-succinamide $N^1$-(2,2-Dimethyl-1S-methylcarbamoyl-propyl)-2R-octyl-$N^4$-hydroxy-3S-methoxy-succinamide $N^1$-(2,2-Dimethyl-1S-methylcarbamoyl-propyl)-2R-hexyl-$N^4$-hydroxy-3S-methoxy-succinamide 2R-(3-Biphenyl4-yl-propyl)-$N^1$-(2,2-dimethyl-1S-methylcarbamoyi-propyl)-$N^4$-hydroxy-3S-methoxy-succinamide 2R-(3-Biphenyl4-yl-prop-2-ynyl)-$N^1$-(2,2dimethyl-1S-methylcarbamoyl-propyl)-$N^4$-hydroxy-3S-methoxy-succinamide 2R-[3-(4-Chlorophenyl)-propyl)]-$N^1$-(2,2-Dimethyl-1S-methylcarbamoyl-propyl)-$N^4$-hydroxy-3S-methoxy-succinamide 2R-[3-(4-Chlorophenyl)-prop-2-ynyl)]-$N^1$-(2,2-Dimethyl-1S-methylcarbamoyl-propyl)-$N^4$-hydroxy-3S-methoxy-succinamide $N^1$-(1S-Dimethylcarbamoyl-2,2-dimethyl-propyl)-$N^4$-hydroxy-2R-isobutyl-3S-methoxy-succinamide and salts, solvates or hydrates thereof.

9. $N^1$-(2,2-Dimethyl-1S-methylcarbamoyl-propyl)-$N^4$-hydroxy-2R-isobutyl-3S-methoxy-succinamide or a salt, solvate or hydrate thereof.

10. A pharmaceutical or veterinary composition comprising a compound as claimed in claim 1 together with a pharmaceutically or veterinarily acceptable excipient or carrier.

11. A pharmaceutical or veterinary composition as claimed in claim 10 wherein the composition is in an orally administrable form.

\* \* \* \* \*